United States Patent [19]

Behnke, III et al.

[11] Patent Number: 5,575,317

[45] Date of Patent: Nov. 19, 1996

[54] SAMPLE TAP APPARATUS WITH PRESSURE SENSITUVE CAP

[76] Inventors: Henry J. Behnke, III, 4 W. Kincaid, Cranbury, N.J. 08512; A. Eric Jansen, Terbreqseweg 124, 3056 JX, Rotterdam, Netherlands; Martin Bal, 3023 Kenross, Houston, Tex. 77043

[21] Appl. No.: 379,187

[22] Filed: Jan. 27, 1995

[51] Int. Cl.⁶ .................................................. G01N 1/100
[52] U.S. Cl. ........................ 141/372; 141/94; 141/383; 138/89; 220/203.22; 220/316; 73/863.86; 73/864.51
[58] Field of Search .................................. 141/370, 372, 141/383, 384, 94, 89–92; 138/89, 96 T; 220/203.22, 316, 303; 73/863.81, 863.85, 863.86, 864.51

[56] References Cited

U.S. PATENT DOCUMENTS

| | | | |
|---|---|---|---|
| 987,518 | 3/1911 | Wendling | 141/384 X |
| 1,363,480 | 12/1920 | Murphy | 141/372 |
| 1,515,026 | 11/1924 | Frauenfelder | 141/384 |
| 2,866,473 | 12/1958 | Schutter | 141/384 X |
| 3,451,589 | 6/1969 | Lee | 220/203.22 |
| 3,893,487 | 7/1975 | Engelking | 138/89 |
| 4,444,331 | 4/1984 | Lankston | 220/316 X |
| 4,534,494 | 8/1985 | Hautiemont | 141/91 X |
| 4,665,960 | 5/1987 | Brzezicki et al. | 141/384 |
| 5,095,958 | 3/1976 | Tincati | 141/91 |
| 5,127,276 | 7/1992 | Prentiss | 73/863.86 |
| 5,209,456 | 5/1993 | Chronister | 141/383 X |
| 5,408,890 | 4/1995 | Klaus | 73/863.81 |
| 5,442,968 | 8/1995 | Westlake, III et al. | 73/863.81 X |
| 5,452,819 | 9/1995 | Vance | 220/303 |

FOREIGN PATENT DOCUMENTS 1581332  12/1980   United Kingdom ................... 220/316

*Primary Examiner*—J. Casimer Jacyna
*Attorney, Agent, or Firm*—Mathews, Woodbridge & Collins

[57] ABSTRACT

A tap to a process fluid line includes a pressure sensitive cap. The force necessary to remove the cap on the tap is directly proportional to the pressure buildup inside the cap so that an operator can take safety measures before removing the cap. The tap includes a base having a first set of reusable threads thereon and a cap having a second set of reusable threads therein which engage with the first set of threads on the base. A hollow fill tube communicates fluid from the process fluid line through a ball valve to a sample bottle when the cap is removed. The resistance provided by the reusable threads is linear and consistent throughout the entire threading and unthreading procedure. In this manner the force necessary to remove the cap is proportional to the pressure buildup inside of the cap. A helical spring is attachable by an anchor to the fill tube and can be employed to steady the mouth of the sample bottle as it is filled by the fill tube. The invention helps to prevent industrial accidents by minimizing the hazard of sample fluid spills and by warning the operator of the buildup of dangerous pressure inside the cap prior to its removal.

6 Claims, 5 Drawing Sheets

SAMPLE TAP APPARATUS WITH PRESSURE SENSITUVE CAP

BACKGROUND OF THE INVENTION

1. Field of the Invention

The invention relates to a sampling tap apparatus in which a sample bottle is filled through a tap which includes a base and a pressure sensitive removable cap.

2. Description of Related Art

There are a number of known prior art approaches for tapping a fluid line. For example, a simple plug could be employed, but plugs tend to wear out rapidly and can be messy to use. A plug would pose a major problem if the materials being sampled were environmentally dangerous.

A second option might be to employ a second valve in a fluid sample line. Valves, however, also have the tendency to wear out and frequently get stuck in either the open or closed position if the materials employed are viscous.

One other possibility would be that if a flanged valve were used, a blind flange could be used to cap or seal off the outlet of the valve downstream from the process side of the system. A blind flange, however, would be somewhat impractical for a typical sampling application because there are generally four bolts that would have to be dealt with in order to remove or install a flange.

There are other problems with prior art approaches such as described above. If a ¼" valve and a ¼" pipe plug were placed together they might meet the requirements set out in the U.S. Clean Air Act (CAA). However, it would be difficult to install the device and then to remove the ¼" pipe plug from the valve each and every time the sample had to be taken. Conversely, if two valves were used in series, it would still be necessary to add some sort of tube or pipe nipple that would direct the fluid flow into the sample bottle and the cost of that would probably exceed the cost of the present invention.

In addition to the foregoing, none of the prior art devices described above are especially responsive to pressure buildup inside the sample line. In other words, the effort to remove a plug or turn a valve according to the prior art techniques would be relatively independent of the pressure in the sample line. Accordingly, the operator would have no warning of potential dangerous pressure buildup.

In summary, the prior art does not appear to teach or suggest an inexpensive sample tap apparatus which includes a cap having reusable threads and which is sensitive to pressure buildup in the sample pipe.

SUMMARY OF THE INVENTION

Briefly described, the invention comprises a sampling tap apparatus in which the force necessary to remove the cap is proportional to the buildup of pressure inside of the tap. A manually operated valve is connected to a process line at one end and to the sample tap apparatus at the other. The base of the sample tap apparatus includes a fill tube which communicates with the control valve at one end and selectively with a sample bottle at the other. In an alternative embodiment, a helical spring shaped guide is attached to the fill tube and serves to help hold the mouth of the sample bottle in position when it is being filled.

A reusable cap includes internal threads that mate with external threads on the base. The threads are linear in the sense that the distance between flights remains constant from beginning to end. In that way the threads never bind and the cap is always reusable. In addition, and most importantly, the pressure necessary to unscrew the cap is constant throughout the threading and unthreading operation so that the operator is aware of any pressure buildup inside of the sample tap apparatus. This can be very critical if pressure inside the sample apparatus has built up to dangerous levels. An alternative embodiment of the cap includes a cavity having a resilient plug therein for sealing the open end of the fill tube and preventing unnecessary leakage. A security cable attaches the sample fill line to the reusable cap so that the cap does not become lost or damaged.

These and other features of the invention may be more fully understood by reference to the following drawings.

DETAILED DESCRIPTION OF THE INVENTION

During the course of this description like numbers will be used to identify like elements according to the different views that illustrate the invention.

Figure 1:
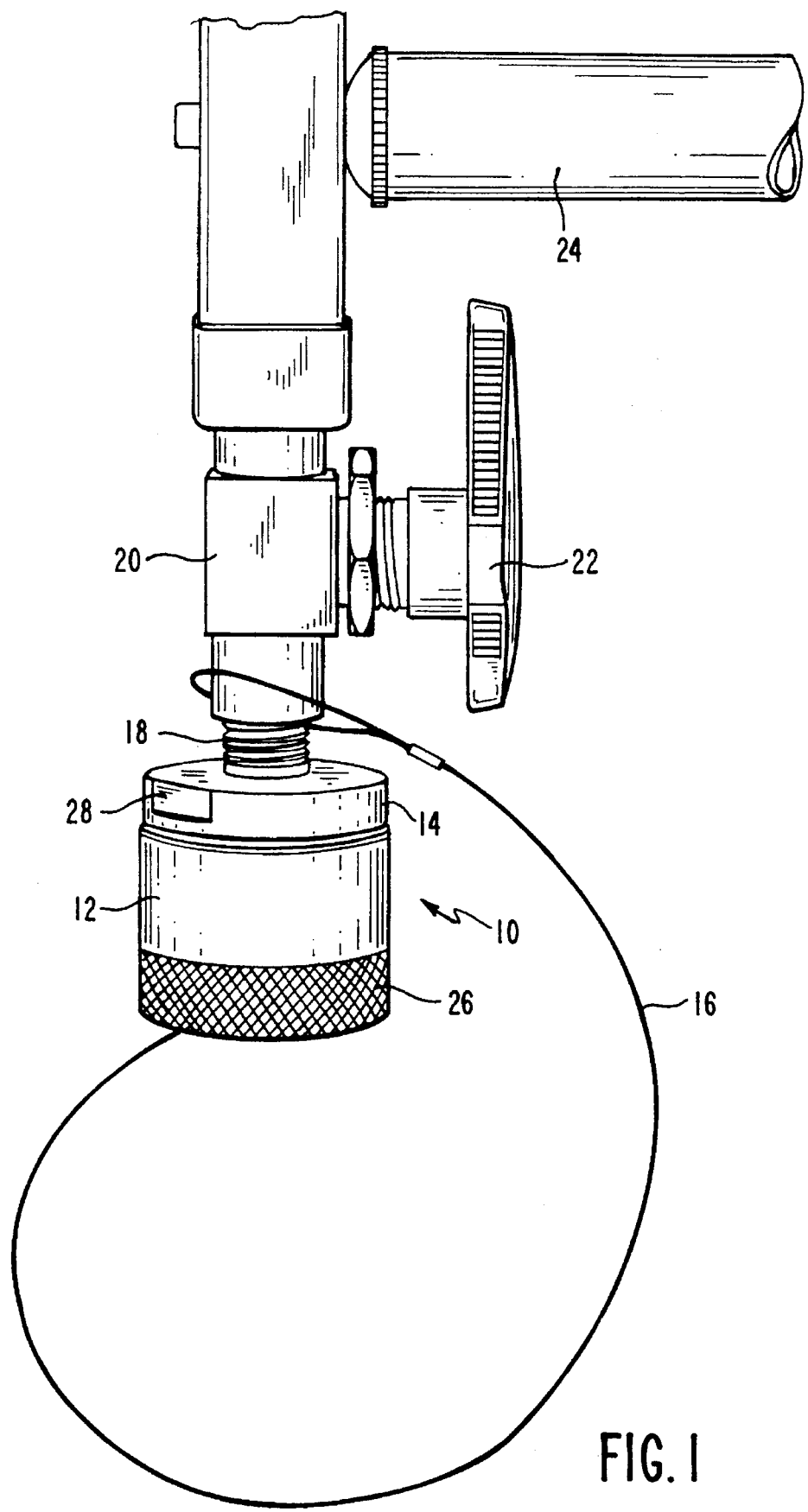
FIG. 1 illustrates the sample tap apparatus according to the preferred embodiment of the invention in its closed state as connected to a process line.

The sample tap apparatus 10 according to the preferred embodiment of the invention is illustrated in its closed state in FIG. 1. Sample tap apparatus 10 includes a reusable cap 12 that includes internal threads which engage with a second set of threads on a base 14. Security cable 16 connects cap 12 to the threaded connector 18 in the base 14 to prevent the cap 12 from becoming lost or damaged. Threaded connector 18 connects base 14 to the downstream end of valve 20. Valve 20 is connected at the other end thereof to a process line 24. A handle 22 controls the opening and closing of valve 20 in the conventional manner. Knurling hash marks 26 on cap 12 make it possible for an operator to manually thread or unthread the cap 12. Knurling 26 also makes it possible for the operator to have a better "feel" of the pressure buildup, if any, inside the sample tap apparatus 10. Wrench flats 28 on base 14 make it possible for an installer to easily connect the sample tap apparatus 10 to valve 20.

Figure 2:
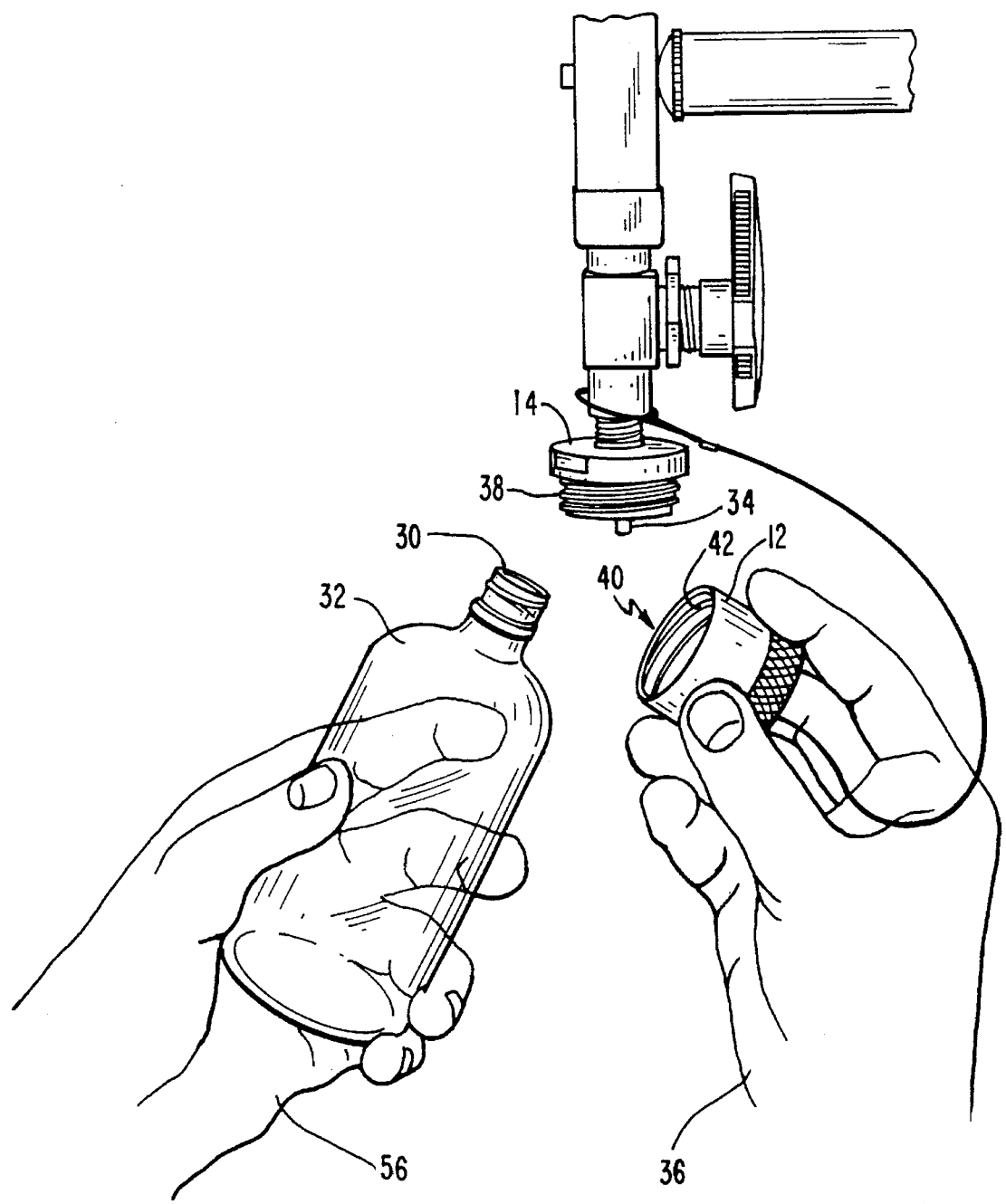
FIG. 2 illustrates the first step in the sampling process in which the sample cap has been removed and a sample bottle is about to be placed in position under the fill tube.

FIG. 2 illustrates the manner in which the cap 12 is readily removed from the base 14 prior to the filling of a sample bottle 32. Sample bottle 32 includes a mouth 30 that fits over the fill tube 34 of the sample tap apparatus 10. Typically, an operator would remove the cap 12 using one hand 36 while holding the sample bottle 32 in the other hand 56. As shown in FIG. 2, the cap 12 has an inside 40 which includes threads 42 which mate with threads 38 on base 14. According to the preferred embodiment of FIGS. 1–3, the fill tube 34 comes close to, but does not touch, the bottom of cap cavity 40 when the cap 12 is fully screwed onto base 14. Threads 42 are linear and not tapered as found with conventional threads. As is clear from FIGS. 1–5, the cap 12 and the base 14 are symmetrical and, therefore, enjoy a common axis or center line. Threads 42 are linear in the sense that they are parallel to, and equidistant from, the common axis of cap 12 and base 14. Threads 42 are, however, preferably tapered towards the center, or common axis, such that they have a first and a second sidewall that lie in different planes and further include a third surface between the first and second sidewalls that lies in a third plane different than the first and second plane of the sidewalls. This has several advantages. First, the threads are indefinitely reusable because there is no significant wear. Second, and most importantly, any pressure buildup on the inside 40 of cap 12 can be detected by the hand 36 of the operator during the cap removal process. Pressure inside of cap 40 builds up and exerts a force on threads 42 which is substantially directly proportional to the actual pressure inside of the sample tap apparatus 10. Therefore, the operator knows in advance if there might be any danger from an explosion due to the pressure buildup in the sample tap apparatus 10. The preferred dimensions and characteristics of threads 38 and 42 are those that conform to ISO standards 2904 (and ISO 2903) for tolerances. These relatively unique threads are sometimes used on machine tools, such as industrial lathes, where it is desirable to remove the work piece from the machine.

Figure 3:
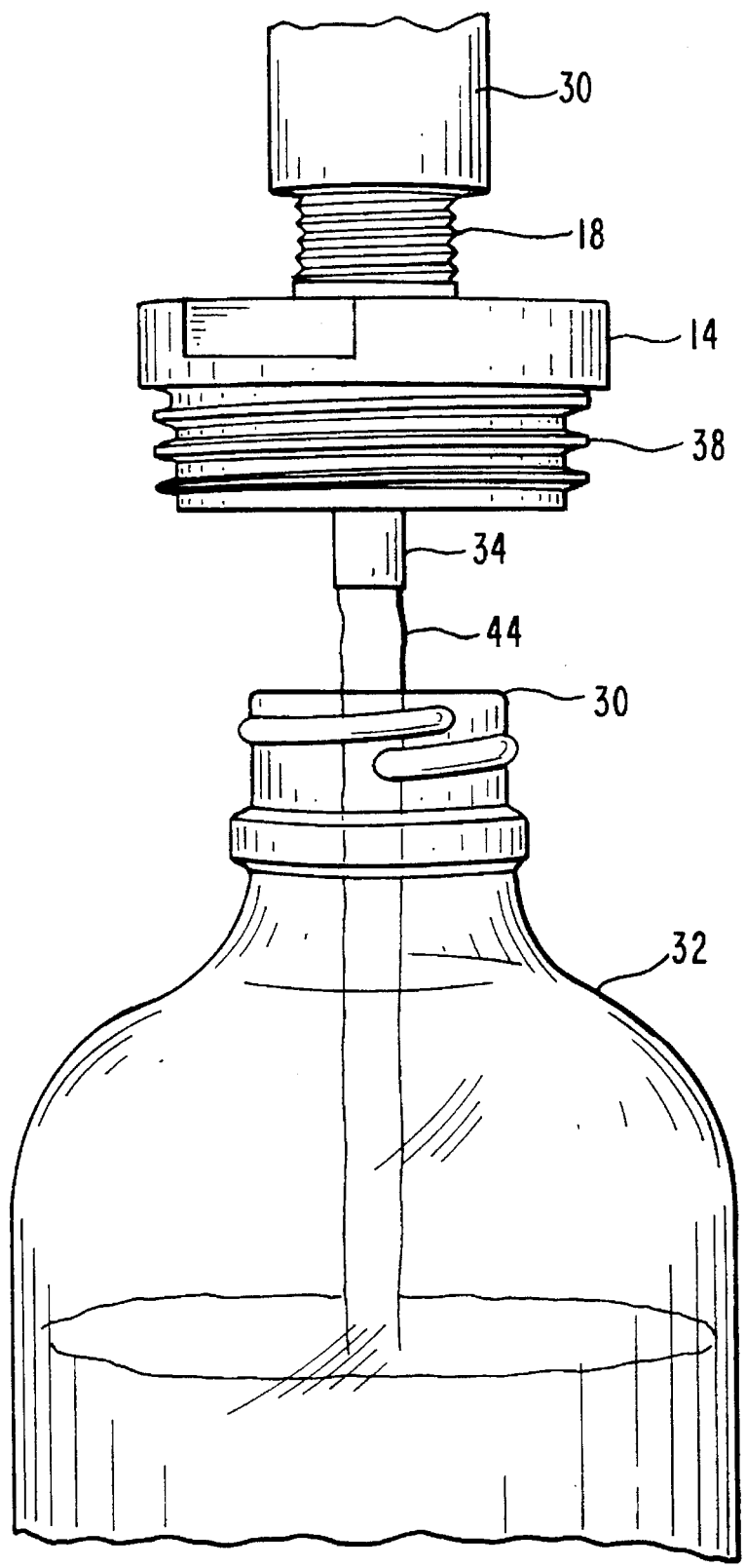
FIG. 3 illustrates a sample bottle being filled by a sample tap apparatus according to the preferred embodiment of the invention.

FIG. 3 illustrates the manner in which a sample bottle 32 is filled once the cap 12 is removed as previously described with reference to FIG. 2. The mouth 30 of sample bottle 32 is placed in the vicinity of the open end of the fill tube 34. A stream of fluid 44 passes from the process line 24 through valve 20, threaded connector 18, base 14 and fill tube 34, into the interior of the sample bottle 32. While the foregoing is satisfactory for many applications, it has been found that the mouth 30 of the sample bottle 32 has to be kept in alignment with the fill tube 34 otherwise the sample stream 44 may splash outside of the sample bottle 32 and injure the operator or contaminate the environment.

Figure 4:
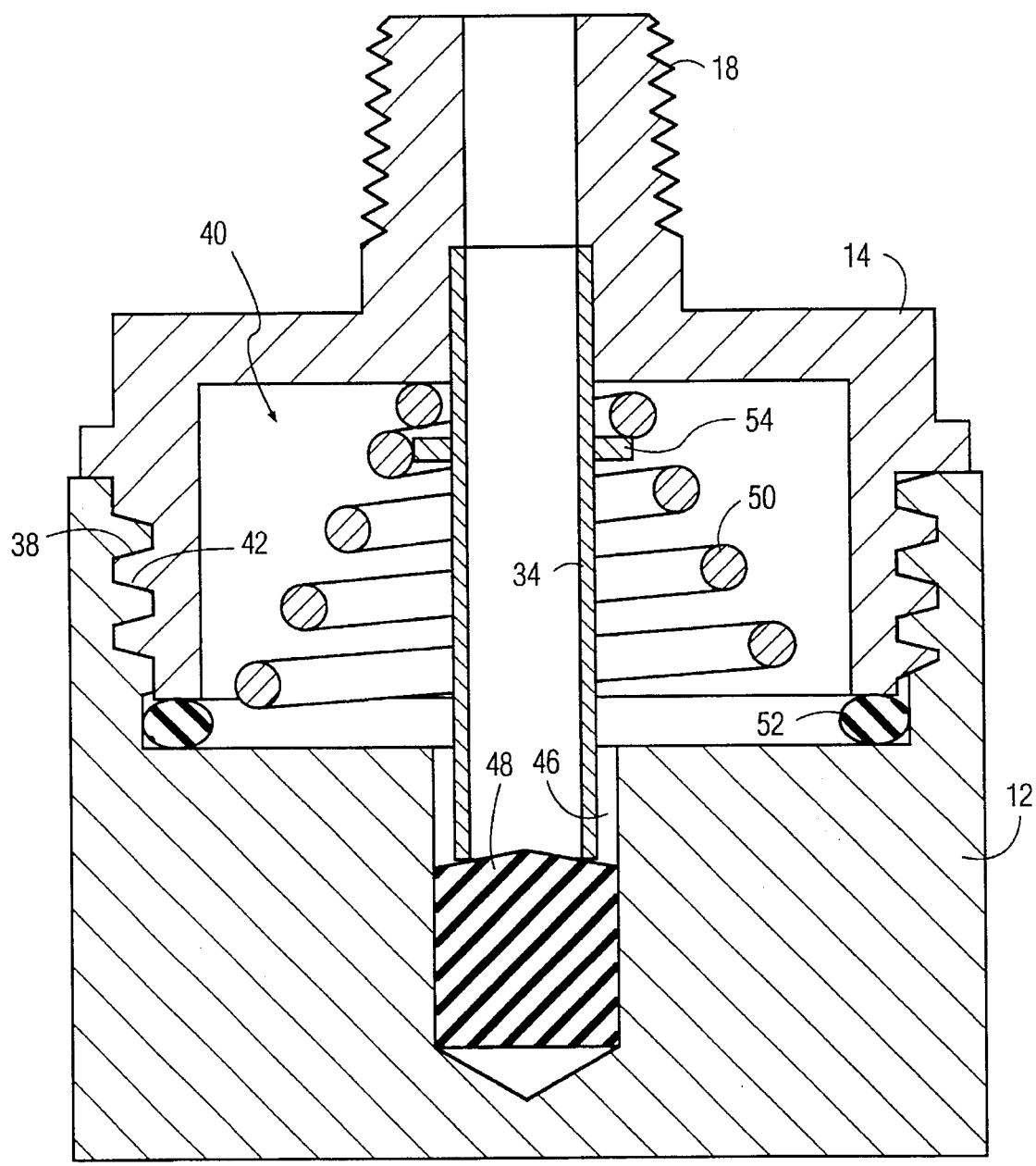
FIG. 4 is a cross-sectional view of an alternative embodiment of the invention in which the cap is illustrated in its closed, engaged position and in which the fill tube includes a helical guide spring for guiding the mouth of the bottle into position under the fill tube.
Figure 5:
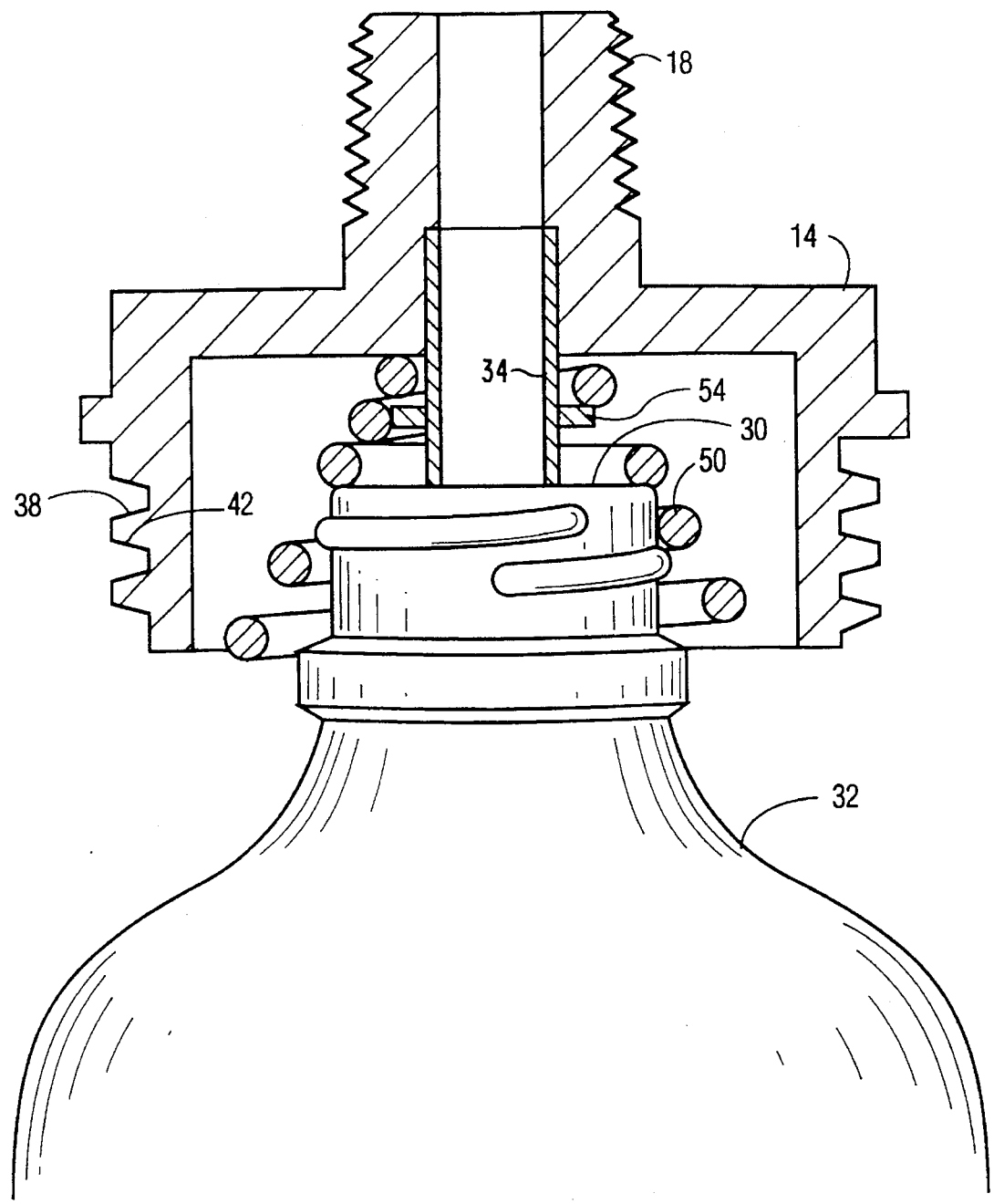
FIG. 5 illustrates the alternative embodiment of the present invention as illustrated in FIG. 4 when the apparatus is employed to fill a sample bottle and the helical spring holds the mouth of the bottle in position under the fill tube.

In order to minimize operator harm and environmental damage, the preferred embodiment of the sample tap apparatus 10 as illustrated in FIGS. 1–3 can be supplied with a helical guide spring 50 and a resilient seal plug 48 as illustrated in the alternative embodiment shown in FIGS. 4 and 5. The preferred embodiment 10 shown in FIGS. 1–3 includes a fill tube 34 that extends down to, but does not touch, the bottom of the cavity 40 in cap 12. This permits pressure to be distributed effectively over the entire interior area 40 of cap 12. The alternative embodiment of FIGS. 4–5 includes an alternative plug 48 that may be used to seal tube 34 with respect to cap 12. FIG. 4 is a cross-section of the alternative embodiment of the invention showing the cap 12 in its closed and fully engaged position with respect to base 14. The open end of fill tube 34 contacts and engages resilient plug 48 located in an internal cavity 46 in cap 12. Plug 48 helps to seal off the open end of fill tube 34 to prevent leakage of sample fluid 44 and the buildup of pressure within the interior 40 of cap 12. An O-ring seal or gasket 52 further helps to prevent the escape of fluid 44 from the interior cavity 40 of cap 12 to the outside environment. In order to hold the mouth 30 of a sample bottle 32 steady with respect to fill tube 34, the sample tap apparatus 10 is provided with a helical guide spring 50 which is attached at its narrow end by a circular anchor 54 to the upstream end of the fill tube 34. FIG. 5 illustrates how the helical guide spring 50 operates with respect to the mouth 30 of a sample bottle 32. Because guide spring 50 is helical in shape, it guides the mouth of bottle 30 like a funnel over the fill tube 34. The flexibility of spring 50 also permits the operator to hold the sample bottle 32 at a variety of different angles without the bottle becoming misaligned with respect to fill tube 34. Also, spring 50 tends to grab the mouth 30 of bottle 32 and thereby assists the operator in supporting the weight of the sample bottle 32.

It should be clear from the foregoing that the sample tap apparatus 10 according to the preferred and alternative embodiments of the invention has certain advantages over prior art approaches.

First, the sample tap apparatus 10 is relatively inexpensive, completely reusable, and easy to clean and maintain.

Second, because the threads 38 and 42 are linear, the pressure required by an operator to remove cap 12 is substantially directly proportional to the buildup of pressure within the interior 40 of the sample tap apparatus 10. Therefore, the operator has advance warning that the pressure inside the sample tap apparatus 10 may be at dangerous levels and can take appropriate actions to avoid injury or environmental harm. The knurling 26 on cap 12 further enhances the tactile ability of the operator to sense the buildup of dangerous pressures within the sample tap apparatus 10.

Third, in order to further assure safety, an alternative helical guide spring 50 is provided to hold the mouth 30 of a sample bottle 32 in proper alignment with regard to fill tube 34 thereby preventing accidental spills.

Fourth, another alternative embodiment calls for a resilient plug 48 to seal the end of fill tube 34 to help prevent leaks inside of cap 12.

While the invention has been described with reference to the preferred embodiment thereof, it would be appreciated by those of ordinary skill in the art that modifications can be made to the structure of the invention without departing from the spirit and scope of the invention as a whole.

We claim:

1. A pressure sensitive tap apparatus for filling a sample bottle wherein said apparatus is connectable to a valve attached to a fluid line, said apparatus comprising:

a base connectable to said valve, said base having a first set of threads thereon;

a fill tube having a first and a second end and a channel therethrough, wherein said first end is attached to said base and communicates with said valve attached to said fluid line;

a cap having an outside surface and an interior cavity, said interior cavity including a second set of threads thereon adapted to mate with said first set of threads on said base;

a recessed cavity inside of said interior cavity of said cap;

an elastomeric plug located inside of said recessed cavity; and, knurling on said outside surface of said cap, wherein the resistance provided by said first set of threads acting against said second set of threads as said cap is screwed onto and off of said base is substantially linear at all times so that the force necessary to unscrew said cap is substantially proportional to the pressure buildup inside of said interior cavity of said cap and wherein said knurling improves the ability of an operator to screw said cap on and off of said base and, further, wherein said second end of said fill tube comes into contact with said elastomeric plug when said cap is screwed onto said base.

2. The pressure sensitive tap apparatus of claim 1 further comprising:

a spring attachable to said fill tube, wherein said spring guides and holds the mouth of said sample bottle as it is filled from said fill tube after said cap has been removed.

3. The pressure sensitive tap apparatus of claim 2 further comprising:

anchor means affixed to said fill tube for attaching said spring to said fill tube.

4. The pressure sensitive tap apparatus of claim 3 wherein said spring has a helical shape and a first and a second end and wherein said first end is attached to said fill tube by said anchor means.

5. The pressure sensitive tap apparatus of claim 4 further comprising:

a security cable means for attaching said base to said cap.

6. The pressure sensitive tap apparatus of claim 5 wherein said cap and base threads substantially conform to ISO 2904 as those standards existed on Jan. 27, 1995.

* * * * *